(12) United States Patent
Misczynski et al.

(10) Patent No.: US 7,254,439 B2
(45) Date of Patent: *Aug. 7, 2007

(54) METHOD AND SYSTEM FOR CONTACTLESS EVALUATION OF FATIGUE OF AN OPERATOR

(75) Inventors: Dale Julian Misczynski, Austin, TX (US); Vladislav Bukhman, East Northport, NY (US)

(73) Assignee: Monebo Technologies, Inc., Austin, TX (US)

( * ) Notice: Subject to any disclaimer, the term of this patent is extended or adjusted under 35 U.S.C. 154(b) by 254 days.

This patent is subject to a terminal disclaimer.

(21) Appl. No.: 11/020,785

(22) Filed: Dec. 22, 2004

(65) Prior Publication Data
US 2005/0148894 A1 Jul. 7, 2005

Related U.S. Application Data

(60) Provisional application No. 60/534,570, filed on Jan. 6, 2004.

(51) Int. Cl.
*A61B 5/05* (2006.01)

(52) U.S. Cl. .............. 600/513; 340/575; 340/576; 180/272

(58) Field of Classification Search .......... 340/575, 340/576; 600/9, 13, 15, 300, 407, 411, 421, 600/422, 481, 483; 180/272
See application file for complete search history.

(56) References Cited

U.S. PATENT DOCUMENTS

| | | | | |
|---|---|---|---|---|
| 4,706,072 A | * | 11/1987 | Ikeyama | 340/576 |
| 5,813,993 A | * | 9/1998 | Kaplan et al. | 600/544 |
| 6,359,449 B1 | * | 3/2002 | Reining et al. | 324/692 |
| 6,497,658 B2 | * | 12/2002 | Roizen et al. | 600/301 |

* cited by examiner

*Primary Examiner*—Carl Layno
*Assistant Examiner*—Eric D. Bertram
(74) *Attorney, Agent, or Firm*—Winstead, PC

(57) ABSTRACT

The invention relates to a method and device for contactless assessment of fatigue of a user, in particular a vehicle operator. The invention is comprised of a seamless continuous evaluation of cardiac activity variability and uses this data as an input for evaluation and quantitative assessment of sympathetic and parasympathetic activity of the autonomic nervous system, which are reliable markers of the physiological condition of a user. The small device is fixed to a driver's safety belt or embedded in the back of driver's seat without direct contacts to a user's body. The device continuously monitors the fatigue level of a user and alerts the user if he/she unexpectedly drifts from wakefulness to drowsiness. The invention significantly improves the safety of a vehicle operator.

22 Claims, 13 Drawing Sheets

METHOD AND SYSTEM FOR CONTACTLESS EVALUATION OF FATIGUE OF AN OPERATOR

CROSS REFERENCE TO RELATED APPLICATIONS

This patent application is based upon Provisional Patent Application Ser. No. 60/534,570 filed on Jan. 6, 2004.

BACKGROUND OF THE INVENTION

The present invention relates to the field of determining and evaluation of fatigue of a user, in particular to evaluation of fatigue of a vehicle driver and alerting the driver if the driver drifts from wakefulness to drowsiness.

The National Sleep Foundation's (NSF) 2002 Sleep in America poll shows that more than one-half of the adults in this country admit to driving while drowsy; seventeen percent say they actually fell asleep at the wheel in the past year.

The National Highway Traffic Safety Administration (NHTSA) conservatively estimates that 100,000 police-reported crashes are the direct result of driver fatigue each year, representing more than 1,550 deaths, 71,000 injuries, and $12.5 billion in economic costs. Studies show that young adults between the ages of 16 and 29 are the most likely to drive while drowsy. However, shift workers, commercial drivers, and people with untreated sleep disorders such as sleep apnea are also at higher risk.

Many physiological measures have been examined in earlier studies as predictors or indicators of driver fatigue.

An increased percentage of eyelid closure is one of the most reliable predictors of the onset of sleep. However, a camera and demanding eye-tracking software must be used to measure this percentage.

Spectral electroencephalogram (EEG) analysis is the most appropriate method for detecting the onset and different stages of sleep. But, this method is useful in laboratory settings only and in a large degree depends on the person's individual physiological factors.

The correlation between heart rate variability and fatigue is a proved fact, but it is difficult to implement in a real world environment. The change in skin potentials during the drift from alertness to drowsiness is a very challenging idea, but there are no reliable correlations still found. There are numerous methods of monitoring driver-vehicle relations as predictors of fatigue, but they are complicated and prone to false alarms.

The present invention offers an effective method and apparatus for monitoring the fatigue level of a driver and alerting the driver, or others, if the driver drifts to a predetermined state of drowsiness.

SUMMARY OF THE INVENTION

Figure 1A:
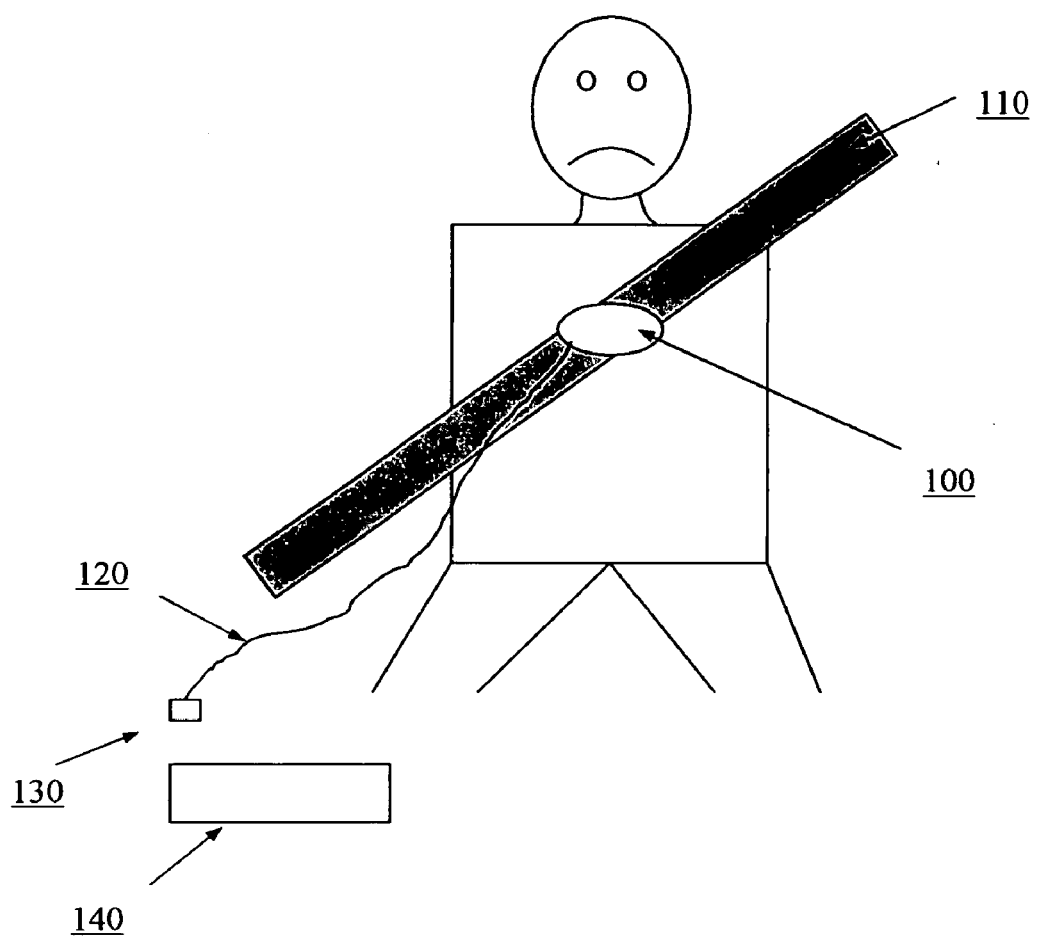
FIG. 1a-1b show the fatigue evaluation device fixed to the vehicle safety belt or imbedded inside of the back of a vehicle seat.

In the following description, numerous specific details are set forth to provide a thorough understanding of the present invention. However, it will be obvious to those skilled in the art that the present invention may be practiced without such specific details. For the most part, details concerning specific non-essential materials and the like have been omitted inasmuch as such details are not necessary to obtain a complete understanding of the present invention and are within the skills of persons of ordinary skill in the relevant art.

The fundamental aspect of the invention is the real-time contactless monitoring and evaluation of the fatigue of the driver incorporated in a portable device fixed to the vehicle's safety belt or embedded in the back of the driver's seat.

These objectives are reached by monitoring cardiac activity variability and quantitative assessment of fatigue level, where cardiac activity signals derive from electromagnetic inductance device without electrodes contacted to the body of the user.

Cardiac activity is mainly conditioned by heart rate and stroke volume. Heart rate is defined as a number of beats per minute, while stroke volume is defined as the volume of blood in millimeters (ml) ejected from the heart due to contraction of the left ventricular.

In the present disclosure, cardiac activity (CA) is defined as a cumulative index in normalized units of the stroke volume (SV) and the heart rate (HR).

Heart rate and stroke volume are not the same for each cardiac cycle (beat). The rate and volume vary from beat to beat. This fluctuation is controlled by sympathetic and parasympathetic branches of the autonomic nervous system (ANS) and reflects the individual's capacity to adapt effectively to environmental demands. The parasympathetic and sympathetic divisions of the ANS constantly cooperate, either facilitating or inhibiting cardiovascular functions. There is a direct correlation between variability of heart rate and stroke volume and activity of parasympathetic and sympathetic systems.

During fatigue and transition from wakefulness to drowsing, dramatic changes occur in the functions sympathetic and parasympathetic systems. It has been shown in many studies that during the fatigue there is a decrease in sympathetic activity and an increase in parasympathetic activity. During the transition from wakefulness to drowsing, sympathetic activity decreases from 53±9% of total power to 41±5%, while parasympathetic activity markedly increases from 19±4% to 40±6%.

One of the objectives of the present invention is providing quantitative assessment of sympathetic and parasympathetic activity and their overtime changes by analyzing cardiac activity variability (CAV). This data is used to evaluate the level of fatigue and to detect the transition from wakefulness to the drowsing.

This is a process involving two steps. The first step includes acquisition of signals representing continuous beat-to-beat changes of stroke volume and heart rate and the translation of the data in to meaningful values.

The second step includes the detection, discrimination, and quantitative evaluation of the "fingerprints" of sympathetic and parasympathetic activities by analyzing the variability of cardiac activity.

In the present invention Fast Fourier Transform (FFT) is used for the mathematical transformation of cardiac activity variability data into power spectral density to discriminate and quantify sympathetic and parasympathetic activities. This information is used as an input for evaluation of user's fatigue and stratification of the risk of the drift from the wakefulness to the drowsing.

In the final aspect of the present invention an electromagnetic inductance signal-processing device is disclosed. The signal-processing device comprises excitation and sensor coils, lock-in amplifier, power and ancillary amplifiers, a processor, and memory. The processor controls the lock-in amplifier, performs all tasks associated with spectral density power (SDP) and signal analysis, and run FFT, service and display programs. The device also includes memory for storing all intermediate data and post processing data.

The present invention targets the transportation industry; however the system may be successfully used in other applications requiring continuous vigilance of an operator such as power station operation, traffic management, manually controlled technological processes, etc. There is also potential for the system in the diagnosis and treatment of sleep disorders, which affect almost 10 percent of the population.

DETAILED DESCRIPTION OF THE DRAWINGS

FIG. 1a shows the exemplary fatigue electromagnetic inductance device (FED) 100 fixed to vehicle's safety belt 110 and positioned against driver's chest. The device is connected to a vehicles computer 140 via cable 120 with, for example, the standard RS232 (DB9) connector 130.

Figure 1B:
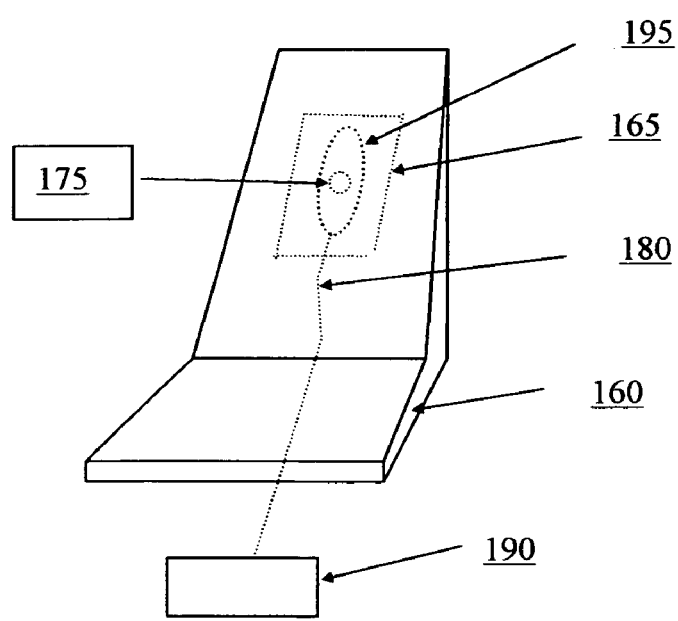

FIG. 1b shows another version of the device 170, which is embedded in the back of driver's seat 160. Cable 180 connects the device with the processor 190 incorporated in vehicle's dashboard. The large size of the excitation coil 165 induces stronger and relatively uniform induction field thus providing a better resolution for sensing coils 175. Instead of wire wound around a core, these flexible sensors use metal lines (or traces) deposited on a flexible plastic-like material, similar to a flexible printed circuit board. Such flexible plastic substrate is produced, for example, by GE Inspection Technologies for eddy current based inspection devices.

The thoracic electromagnetic inductance technology is based on evaluation of cardiac activity by the measurement of fluctuation of eddy current induced in the heart region using an alternating current induced magnetic field. This technology has been used for decades in non-destructive defect control, geophysics, for content measurements and etc. Starting in 1965, this technology has been successfully used in medical applications. Main advantages of magnetic inductance method include:

absence of physical contacts between the body and magnetic inductance device sensors;

the method has high signal to noise ratio compare to methods using contact sensors;

probe current can be induced in the body seamlessly without the screening effect of an insulation layer (clothing) and bones.

Figure 2:
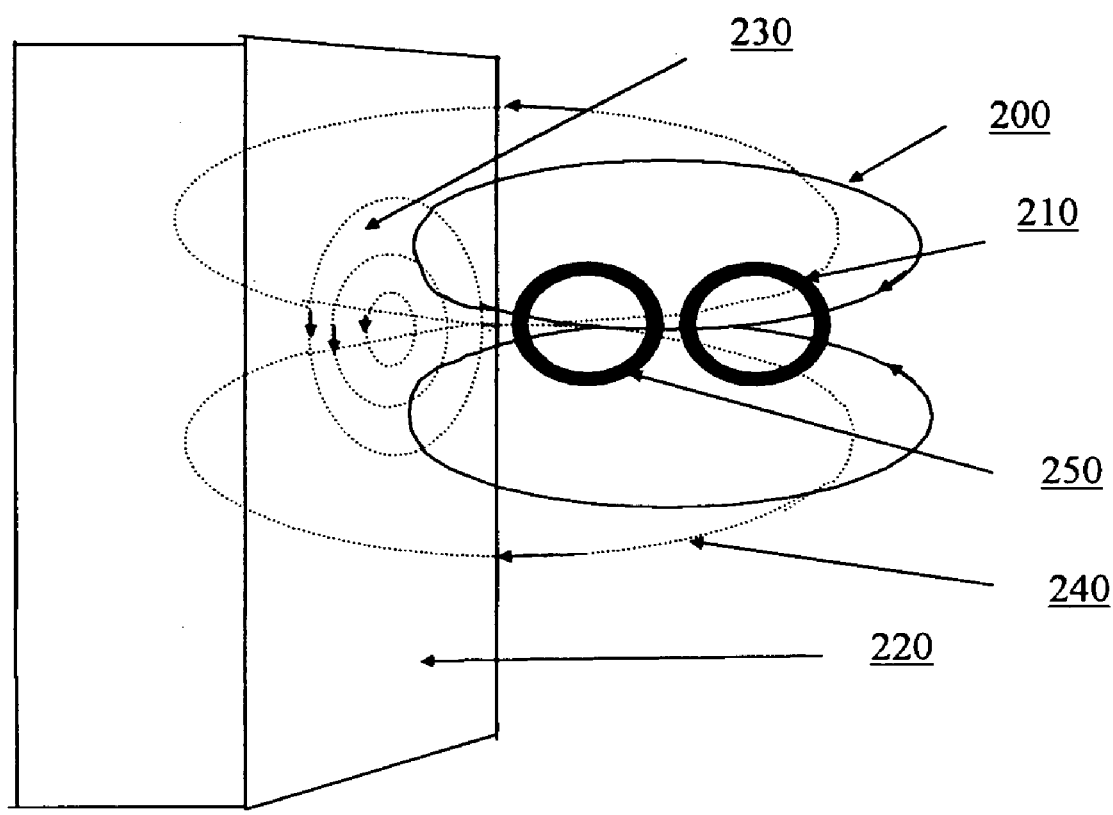
FIG. 2 illustrates the basic principals of electromagnetic inductance method.

FIG. 2 illustrates the basic principles of the thoracic electromagnetic inductance technology. Electromagnetic field 200 of excitation coil 210 induces current in the conductive body 220 proportionally to the conductivity distribution. Current in the body induce the secondary magnetic field 230 which induce 240 current in a receiver coil 250, sensor. Operation of the sensor is based on measuring changes in the amplitude of a marginal RF oscillator, caused by eddy current losses in the heart region. Changes of amplitude reflect changes in heart region energy absorption, which depends on the volume of blood in the heart and heart rate.

Validity studies and clinical trials demonstrated 0 bias between measurements made using electromagnetic inductance technology and measurements performed by invasive and non-invasive medical devices used in clinical practice.

Figure 3:
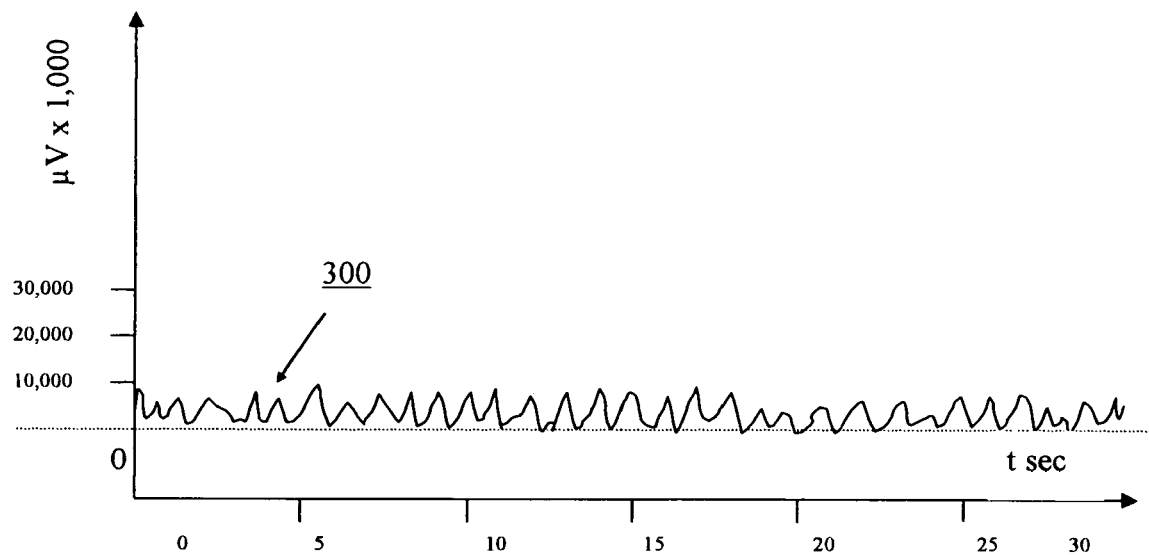
FIG. 3 shows an example of a waveform reflecting changes of cardiac activity recorded by the fatigue evaluation device.

FIG. 3 shows a 30 second sample of CA waveforms performed by hemodynamic monitoring device using electromagnetic inductance technology.

Figure 4:
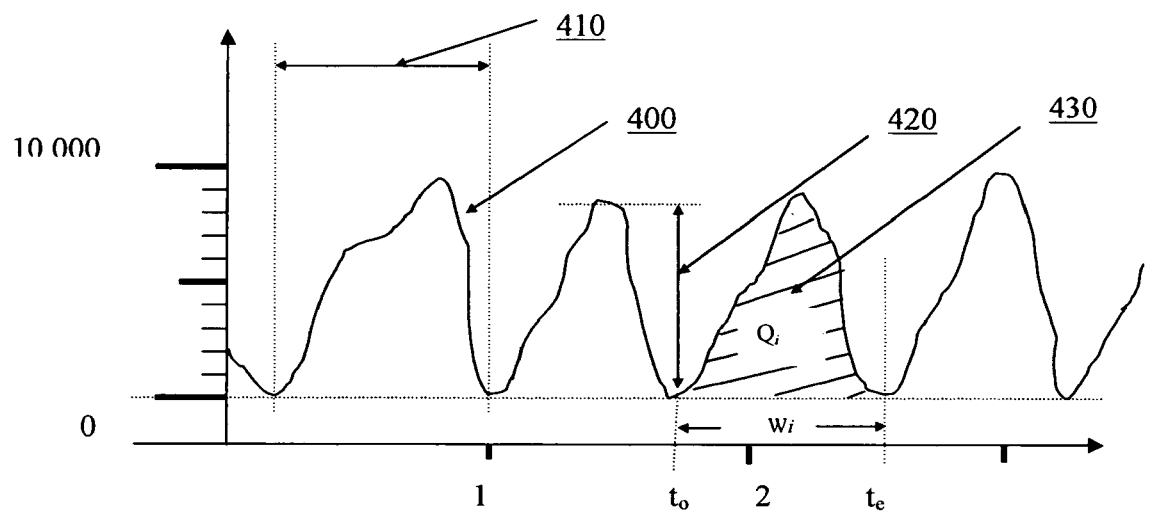
FIG. 4 shows a 3 second fragment of changes of cardiac activity.

FIG. 4 illustrates a 3 second fragment 400 of CA waveform. Width of CA wave 410 reflects the HR at each cardiac cycle that is defined as:

$$HR_i = \frac{60}{W_i} * 1000$$

Where:
$HR_i$=heart rate of cardiac cycle i;
$W_i$=width of wave i in ms.

Magnitude 420 of the wave reflects the stroke volume, while the area below the wave 430 represents the cumulative CA. Area $Q_i$ can be determined by using equation:

$$Q_i = \int_a^b f(x)dx \qquad (1)$$

Where:
a=$t_o$;
b=$t_e$

Because of the discrete nature of analyzed signals, the area $Q_i$ of each CA wave 430 is calculated using equation (2), which is a discrete representation of equation (1).

$$Q_i = \sum_{j=1}^{n} A_j \qquad (2)$$

Where:
$Q_i$=area of CA wave related to cardiac cycle i, $A_j$=amplitude of sample j of CA wave of cardiac cycle i, n=number of samples within cardiac cycle i.

The sampling rate used in the present invention is 128 Hz because sampling in a range of 100 to 250 provides sufficient sensitivity and reproducibility. However, persons of ordinary skill in the art may successfully use other values. The $CA_i$ is equal:

$$CA_i = k * Q_i \text{n.u.} \qquad (3)$$

Where:

k is a normalizing factor for converting calculated value of $Q_i$ in the meaningful value;

$Q_i$=area of wave $W_i$;

n.u. stands for normalized unit.

The measurement of real values of SV and HR is outside the scope of the present invention, because the quantitative evaluation of user's fatigue is based on the variation of CA, which is a cumulative derivative of SV and HR, rather then on SV and HR per se. For this reason factor k is arbitrary and in the present invention k is equal 0.01.

Figure 5A:
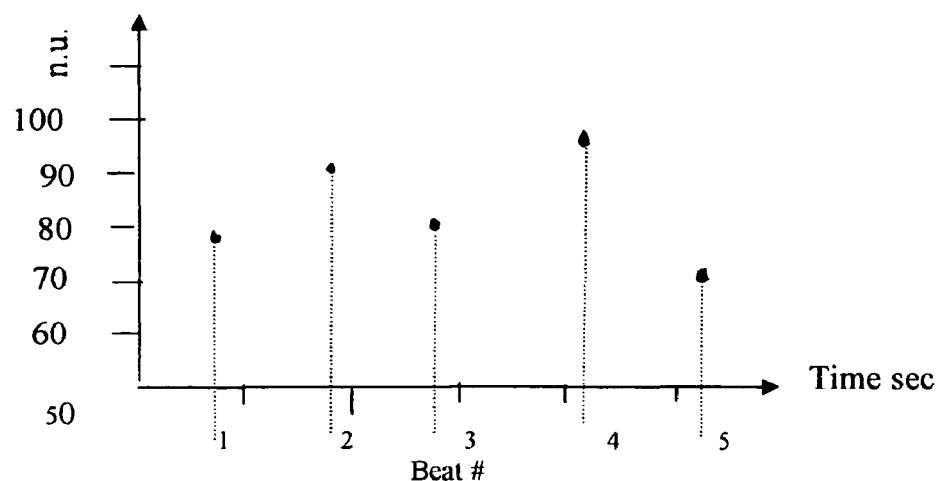
FIG. 5a-5c illustrates time-domain distribution of cardiac activity measured data.

FIG. 5a shows an example of the distribution plot of measured CA of 5 consecutive cardiac cycles (beats). Due to time fluctuation between cardiac cycles, the plot represents irregularly time-sampling signals.

Figure 5B:
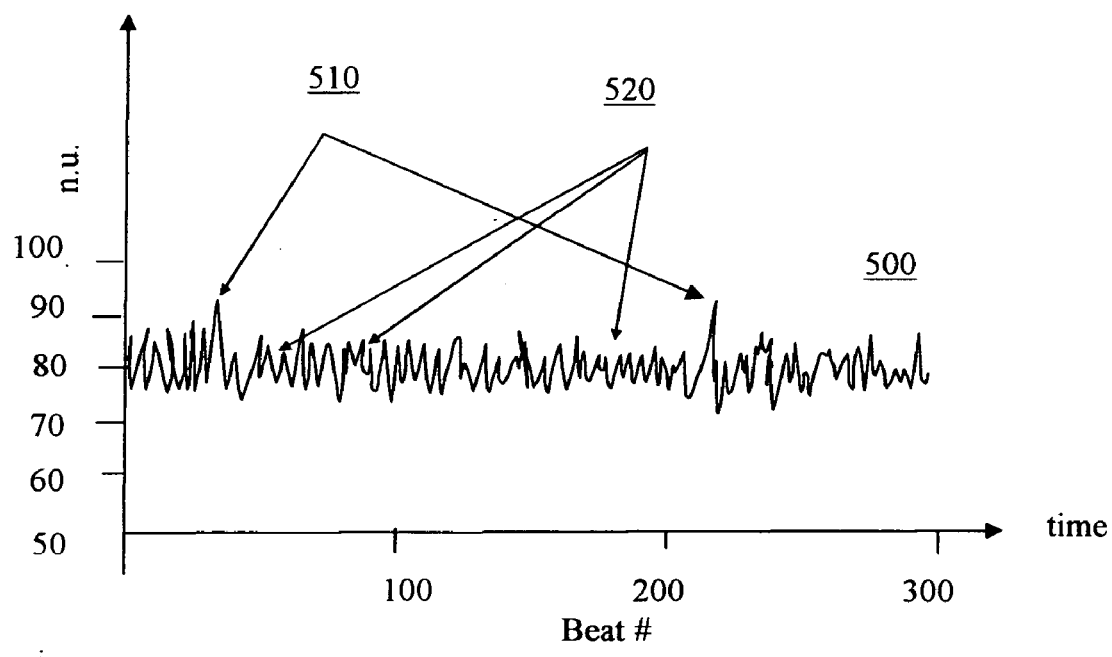

FIG. 5b shows an irregular sampled plot (tachogram) 500 of 300 consecutive $CA_i$ values. The ordinate represents measured values of $CA_i$. Spikes 510 are due to increased sympathetic activity, while low fluctuations area 520 points on prevalence of parasympathetic activity.

Traditional spectral analysis methods are not able to process irregular sampled signals. In the present invention irregular sampled tachogram is resampled using a sampling rate equal to half of the average interval found in the time-domain tachogram. This rate is compliant with Nyquist theorem (i.e. sampling rate is higher than twice the highest frequency contained in the signal) and at the same time it's low enough for effective usage of processing power. However, persons of ordinary skill in the art may successfully use other values.

Figure 5C:
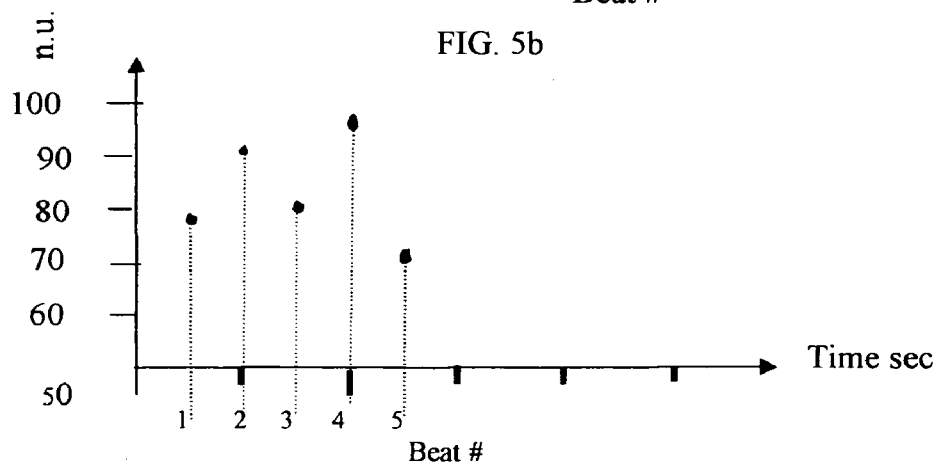

FIG. 5c shows an example of resampling of the tachogram shown on FIG. 5a. Resampled points are repositioned at the new sampling interval equal to the half average interval found in the tachogram shown on FIG. 5a.

The resampled tachogram is used as an input for the Fourier Transform spectral analysis.

Figure 6A:
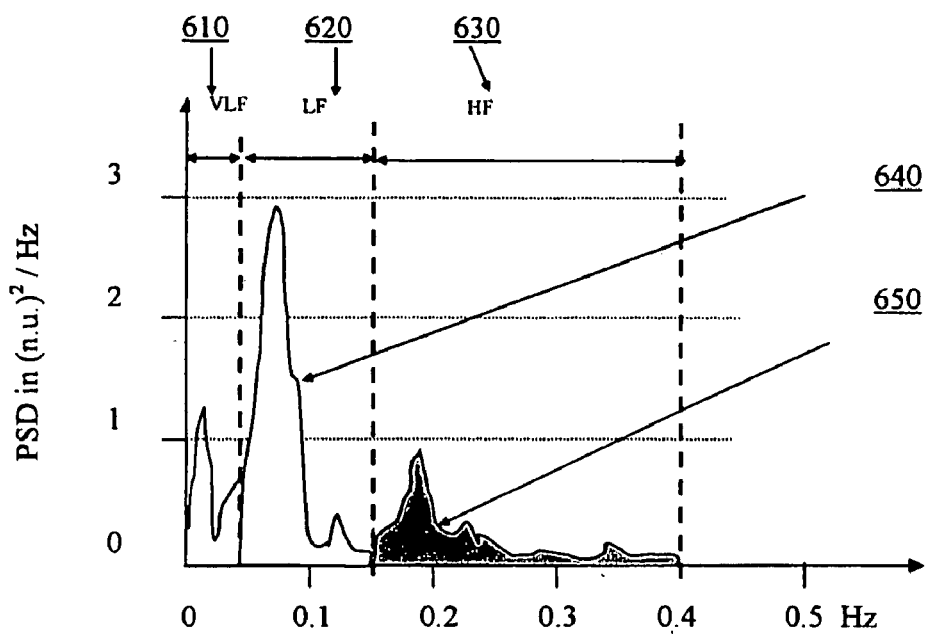
FIG. 6a-6b demonstrates three main spectral components of the variability of the cardiac activity.
Figure 6B:
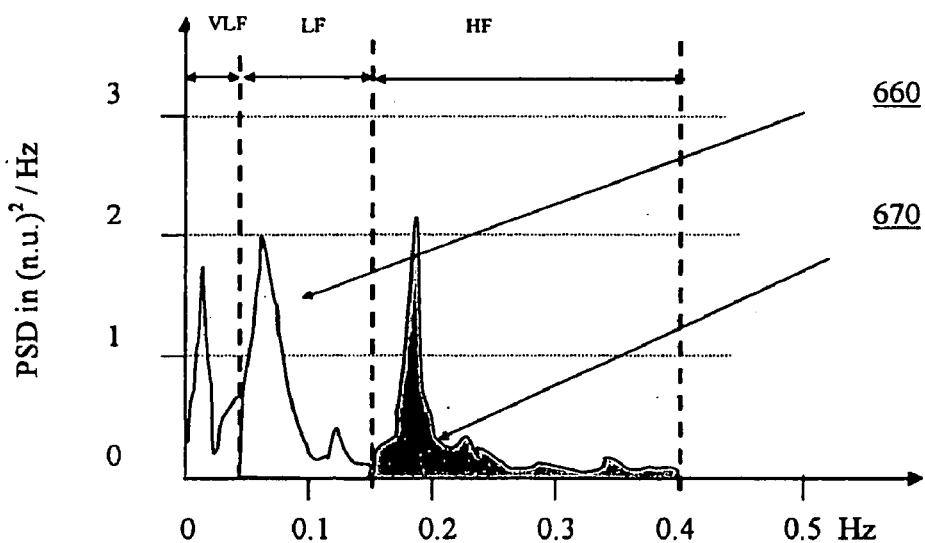

The total power spectrum of CAV resampled tachogram is divided into three main frequencies, FIG. 6a-6b:

the very low frequency range (VLF) less than 0.04 Hz, discriminates slower changes in CAV and reflects sympathetic activity 610;

low frequency range (LF) 0.04 to 0.15 Hz representing both sympathetic and parasympathetic activity 620;

and high frequency (HF) 0.15 to 0.4 discriminates quicker changes in the CA and reflecting parasympathetic activity 630.

The power spectrum division on less than 0.04, 0.04 to 0.15, and 0.15 to 0.4 is defined by a standard developed by *Task Force of European Society of Cardiology and North American Society of Pacing and Electrophysiology, European Heart Journal* (1966), 17, 354-381.

In the present invention, Fast Fourier Transform (FFT) algorithm is applied to evaluate the discrete-time Fourier transform (DFT) of N equispaced samples of a 5-minute time-series of records of CAV. A five-minute time-series is recommended by the standard developed by *Task Force of European Society of Cardiology and North American Society of Pacing and Electrophysiology, European Heart Journal* (1966), 17, 354-38. However, persons of ordinary skill in the art may successfully use other values.

The number of operations required to calculate the FFT is proportional to $\log_2 N$ when N is an integer power of 2. In the present invention N=1024 and covers the maximum possible number of samples of 5 minutes of the time-series. The number of samples is artificially increased by adding zero-value samples (zero-padding), if the number of samples is less than 1024.

Standard, off-the-shelf FFT software is used for calculation of the total spectrum power (TP), power spectrum distribution, and calculation of sympathetic and parasympathetic spectral powers, e.g. FFTW Version 3.0.1, Matlab, The Mathworks. However, persons of ordinary skill in the art may successfully use other FFT software.

FIG. 6a illustrates an example of calculated distribution of power spectrum density (PSD) 640 and 650 for a person in full awake stage.

FIG. 6b shows an example of the calculated power spectrum distribution 660 and 670 when a person drifts to the drowsiness stage. The transition from wakefulness to the drowsing stage is marked by a progressive decrease in LF spectrum power reflecting sympathetic and parasympathetic activities and a significant increase in HF spectrum power reflecting parasympathetic activity.

Figure 7:
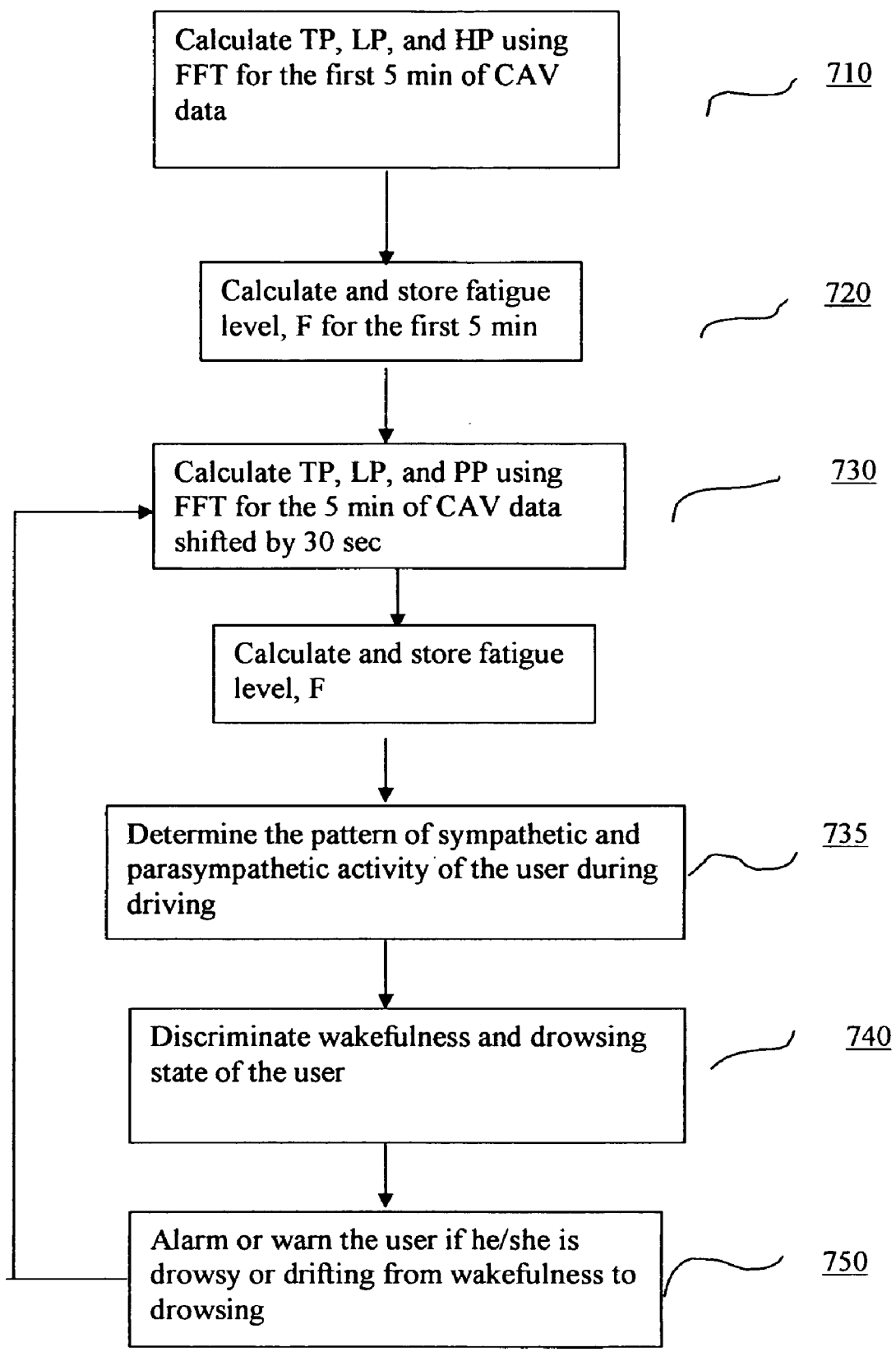
FIG. 7 illustrates steps of fatigue evaluation and alerting the user.

FIG. 7 illustrates steps of fatigue evaluation and alerting of the user.

The first step 710, total power (TP), LF band activity power (LP), and HF band parasympathetic activity power (HP) are calculated for the first 5 minutes of CAV time series using FFT algorithm.

The second step 720, fatigue level F is calculated as ratio of LP to HP.

$$F = \frac{LP}{HP} \qquad (4)$$

Where:

F=fatigue value,

LP=sympathetic activity power,

HP=parasympathetic activity power.

The calculated value F is stored in the FIFO buffer for further analysis.

Figure 8:
FIG. 8 illustrates moving 5-minute intervals of time series.

Next step, 5 minutes time interval is shifted by 30 seconds as shown on FIG. 8, and the new set of TP, LP and HP is calculated 730.

Steps 720 and 730 are repeated for the first 30 minutes of driving (system's warm up time) and then the buffer is updated for each 5 minutes of driving.

Next step, the pattern (signature) of sympathetic and parasympathetic activities of the user during driving are determined 735 using 30 minutes data collected in the buffer. The driving pattern is a mean value $F_m$ of LP to HP ratio within 30 minutes of driving. The pattern, $F_m$ is updated every 5 minutes of driving thus providing adaptation to changing driving environment. 30 minutes of driving is a reasonable time for determining the driving pattern. However, persons of ordinary skill in the art may successfully use other time interval.

The transition from wakefulness to drowsing is characterized by the rapid shift of predominance of sympathetic activity to predominance of parasympathetic activity. Sympathetic power, LP drops up to 10%, while parasympathetic power, LP increases up to 50%. These changes occur during time interval from 1 to 5 minutes.

In the step 740 the system calculates the mean ratio, $F_c$ of sympathetic and parasympathetic activity, LP/HP for the last 5 minutes using data stored in the FIFO buffer and compares $F_c$ with 30 minutes meant value $F_m$ (driving pattern).

If $F_c \leq 0.75 * F_m$, (i.e. ratio of sympathetic activity to parasympathetic activity drops by equal or more then 25% during the last 5 minutes), then the system alarms 750 the user. Persons of ordinary skill in the art may successfully use other time interval and percent decrease.

The system also warns 750 the driver if the driver is drifting from wakefulness to drowsiness. The intensity of warning signal depends on the calculated length of the expected transition time from wakefulness to drowsing. The intensity gradually increases from lowest to highest level reflecting the expected transition time from equal or less than 60 s to less then 5 s.

Figure 9A:
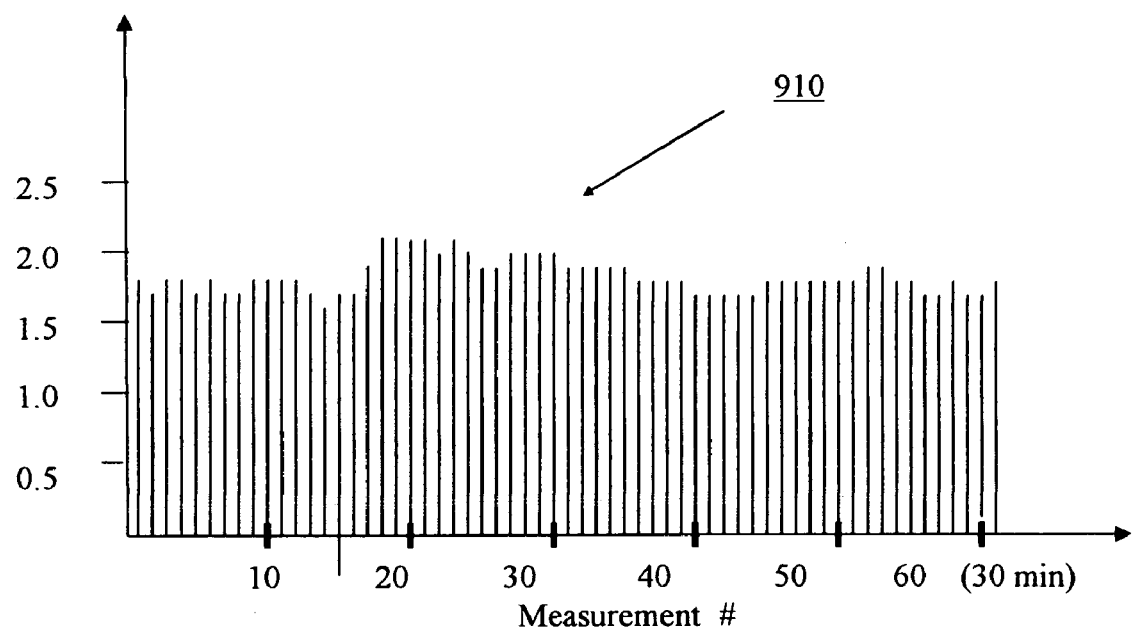
FIGS. 9a and 9b show 30 minutes plots of sympathetic and parasympathetic activities.

FIG. 9a is an exemplary plot 910 of fatigue values, F stored for 30 minutes of driving. In this embodiment abscissa represents each 30 s measurement number performed for 5 min time interval, and ordinate represents correspondent fatigue value, F which is ratio sympathetic power to parasympathetic power, LP/HP.

Figure 9B:
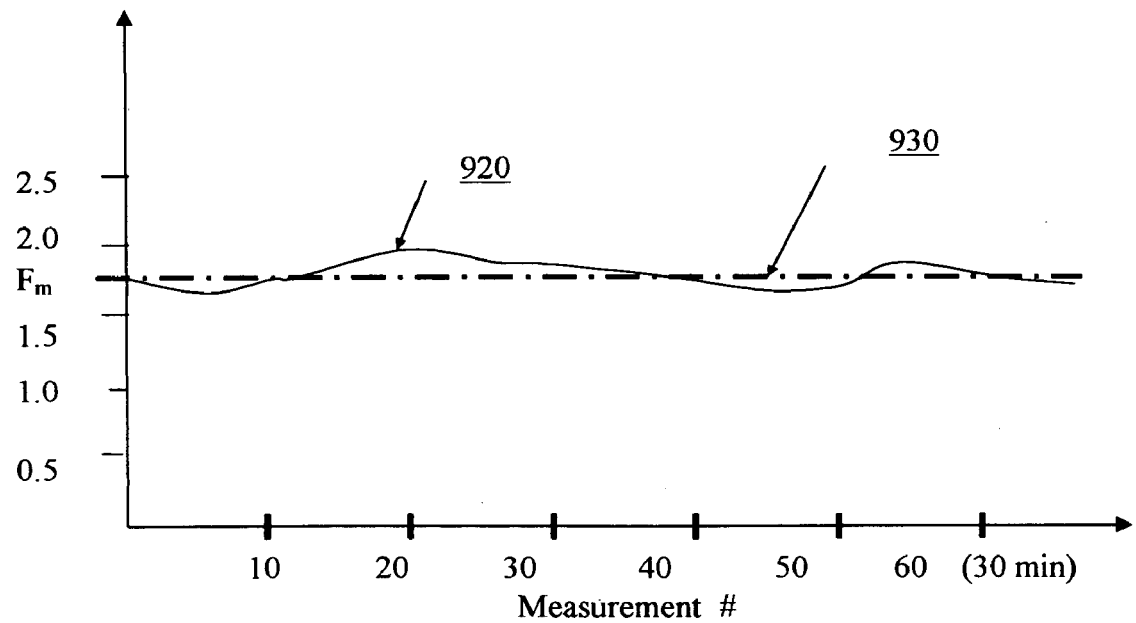

FIG. 9b illustrates a smoothed curve 920 built by extrapolation of the plot shown on FIG. 9a using the triangular smooth method and a standard Matlab's extrapolation routine for discrete signals. However persons of ordinary skill in the art may successfully use other smoothing and extrapolation routines. Line $Y=F_m$, 930 represents the baseline of driving pattern $F_m$.

Figure 10:
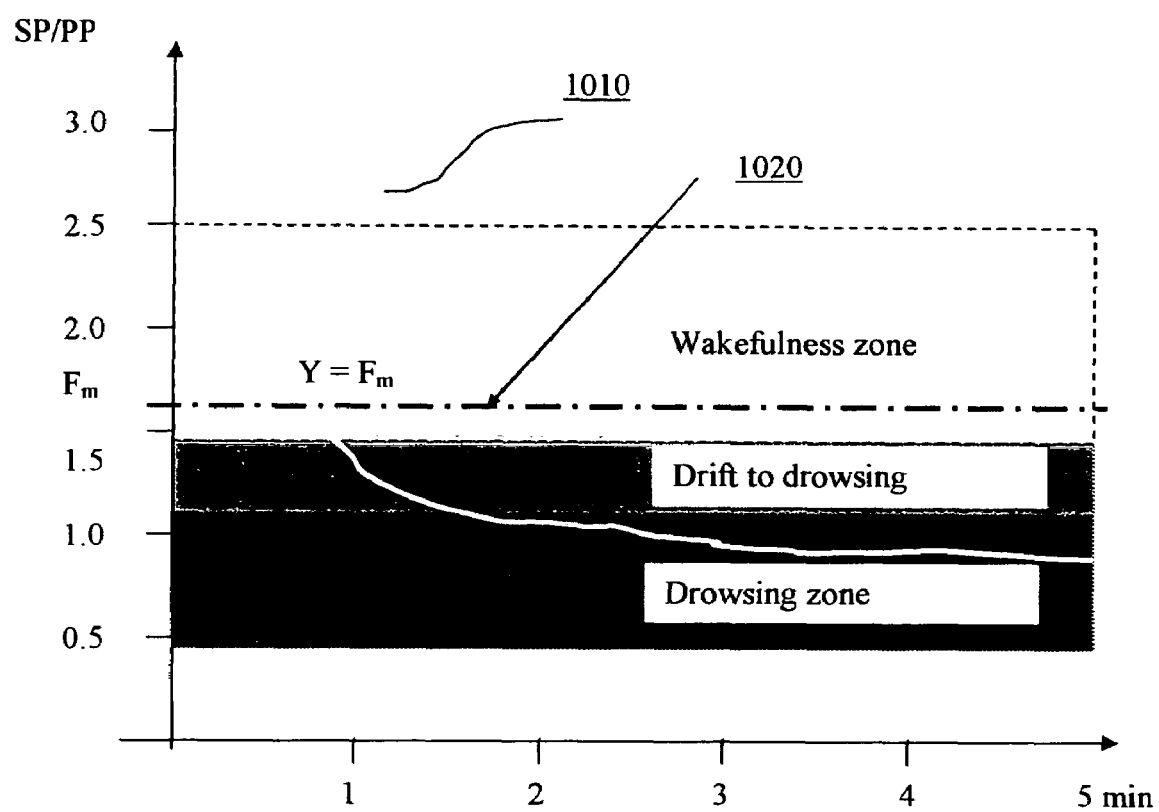
FIG. 10 illustrates an example of the drift of the user from wakefulness stage to drowsing.

An example of the transition 1010 of the user from wakefulness to drowsing is shown in FIG. 10. The ratio LP/HP dropped by more than 25% within less then 4 minutes. The line 1020 shows the baseline of the driving pattern of the driver.

After the testing the driver for the drowsing, the system determines a possibility of drowsing of the driver within next 60 seconds by providing analysis of the baseline driving pattern and extrapolation of the last 5 minutes of driving pattern.

Figure 11:
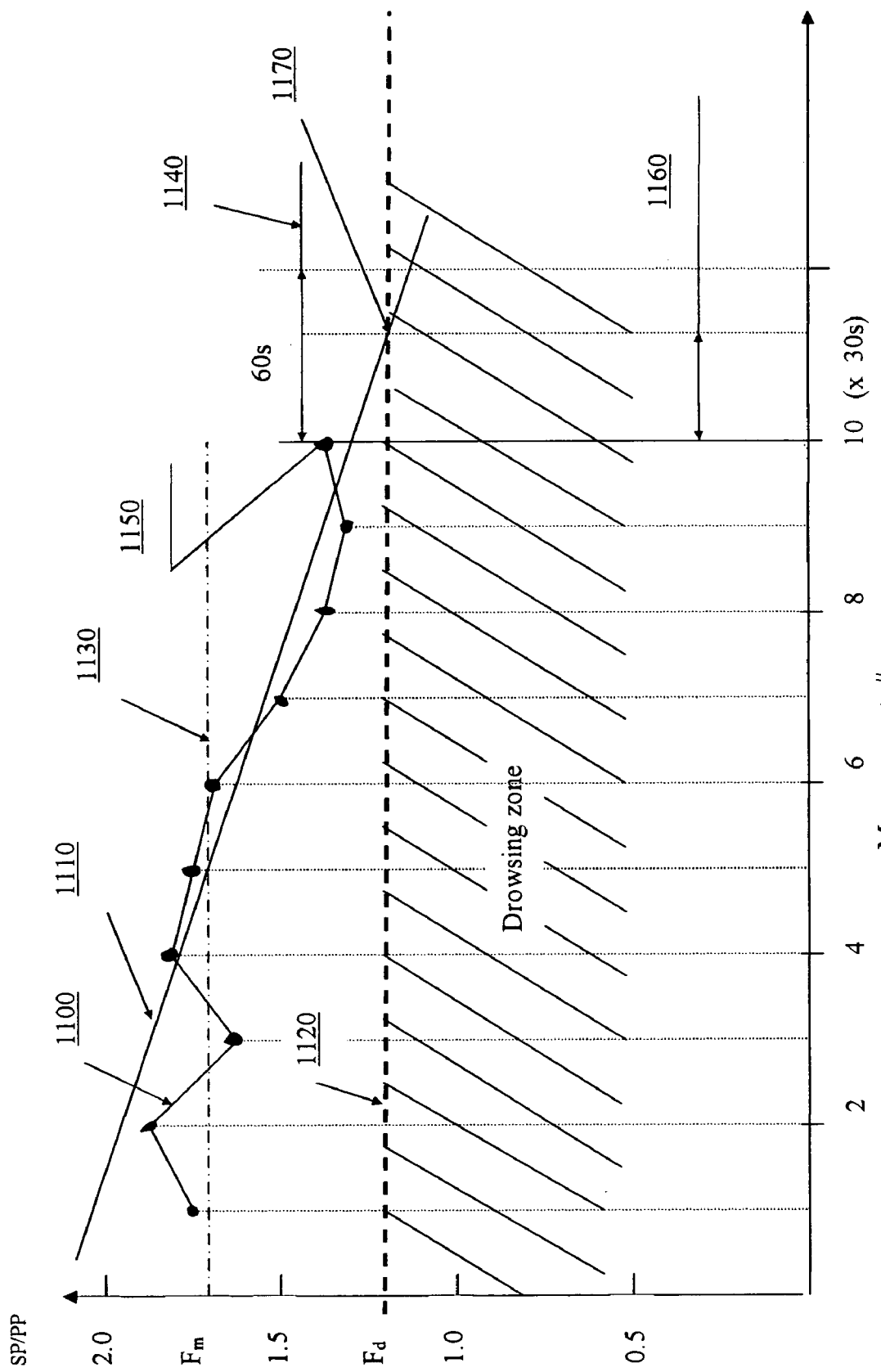
FIG. 11 explains details of the prediction of drowsiness.

FIG. 11 illustrates the determining of the projected values of fatigue level, F within next 60 seconds of driving. 10 last stored values of fatigue level 1100 are smoothed using 9-points triangular smooth method:

$$F_j = \frac{Y_{j-4} + 2Y_{j-3} + 3Y_{j-2} + 4Y_{j-1} + 5Y_j + 4Y_{j+1} + 3Y_{j+2} + 2Y_{j+3} + Y_{j+4}}{25} \quad (5)$$

Where:
$Y_j$=value of measurement j;
j=5 to n−4;
n=10.

The procedure (5) comprises two iterations and transforms the fatigue level waveform 1100 in a vector 1110 representing the tendency of CAV of a current driving pattern of the driver. The iterations j=5, determines the first pair of coordinates of the vector 1110:

$$F_5 = \frac{Y_1 + 2Y_2 + 3Y_3 + 4Y_4 + 5Y_5 + 4Y_6 + 3Y_7 + 2Y_8 + Y_9}{25}$$
$$t = 5$$

The iterations j=6, determines the second pair of coordinates of the vector 1110:

$$F_5 = \frac{Y_2 + 2Y_3 + 3Y_4 + 4Y_5 + 5Y_6 + 4Y_7 + 3Y_8 + 2Y_9 + Y_{10}}{25}$$
$$t = 6.$$

The tendency vector is defined by equation:

$$F = A * t \quad (6)$$

Where:
F=fatigue level;
A=liner coefficient;
t=measurement number.
The threshold line 1120 is defined as:

$$Y = F_d \quad (7)$$

Where:

$$F_d = 0.75 * F_m. \quad (7)$$

$Y = F_m$ 1130 is the baseline of the driving pattern of the driver during last 30 minutes.

If the vector 1110 crosses the threshold line 1120 during 60 seconds 1140 after the last measurement 1150, then the system warns the driver that the driver is possibly drifting to the drowsing stage. The shorter the interval 1160 between crossing 1170 and the last measurement, the more intensive warning signal is provided by the system.

A 60 second advance warning is a reasonable time to avoid a possible accident and not bothering the operator with remote possibilities. However, persons of ordinary skill in the art may successfully use other warning time periods.

Figure 12:
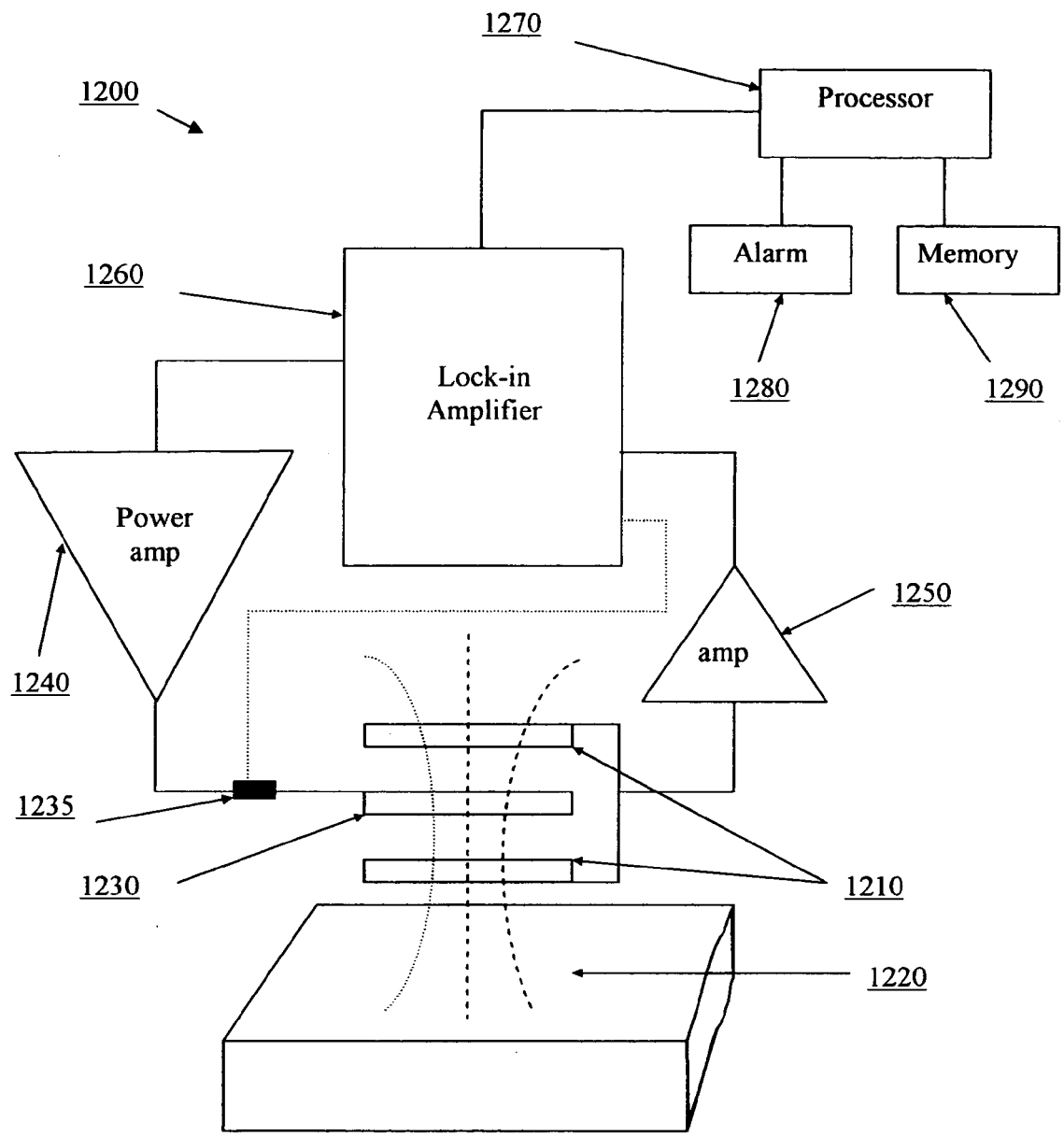
FIG. 12 is a block diagram of an exemplary embodiment of the electromagnetic inductance device for evaluation of fatigue of a user.

The exemplary device 1200 shown on FIG. 12 comprises of 2 sensing coils 1210 for supplying an induced current from the subject without contacting the body 1220; excitation coil 1230 for induction magnetic field into the subject; power amplifier 1240 providing AC current to the excitation coil; amplifier 1250 which serves for reducing an effect of residue voltage; lock-in amplifier for driving the excitation coil; a digital processor 1270 for controlling the lock-in amplifier and analyzing of the digital data of CA waveforms and evaluation the condition of the user; sound alarm unit 1280 for audio alerting the user; and memory 1290 for storing intermediate data during calculation provided by the processor.

Sensing coils 1210 are shielded in order to avoid capacitive effect and positioned from the excitation coil at approximately 5 mm. The distance from the excitation coil 1230 to the body 1220 should be approximately 20 mm.

The power amplifier 1240 uses the oscillator signal from lock-in amplifier 1260 to drive excitation coil 1230. Commercial amplifier PA09, Apex Microtechnology with output current of 500 mA may be used as the power amplifier 1240.

Since the measured signal is relatively small compare to the residual signal, an additional amplifier 1250 is used before providing the signal to the lock-in amplifier for phase detection. The reference signal for phase detection is fed from the resistor 1235. INA 106, Texas Instrument may be used as the amplifier 1250.

Lock-in amplifier 1260 provides oscillator output, phase detection and measurement of the output signal. Single-board lock-in amplifier LIA-BV-150, supplied by FEMTO and operating in a range of up to 150 kHz may be used in the present embodiment.

The processor 1270, controls operation of the lock-in amplifier 1260, hosts and run application FFT routine and provides evaluation of measured parameters and sends the signal to alert the user 990 if the parameters fall outside threshold values. ARM7 processor by ARM Ltd., may be used in the present embodiment.

Figure 13:
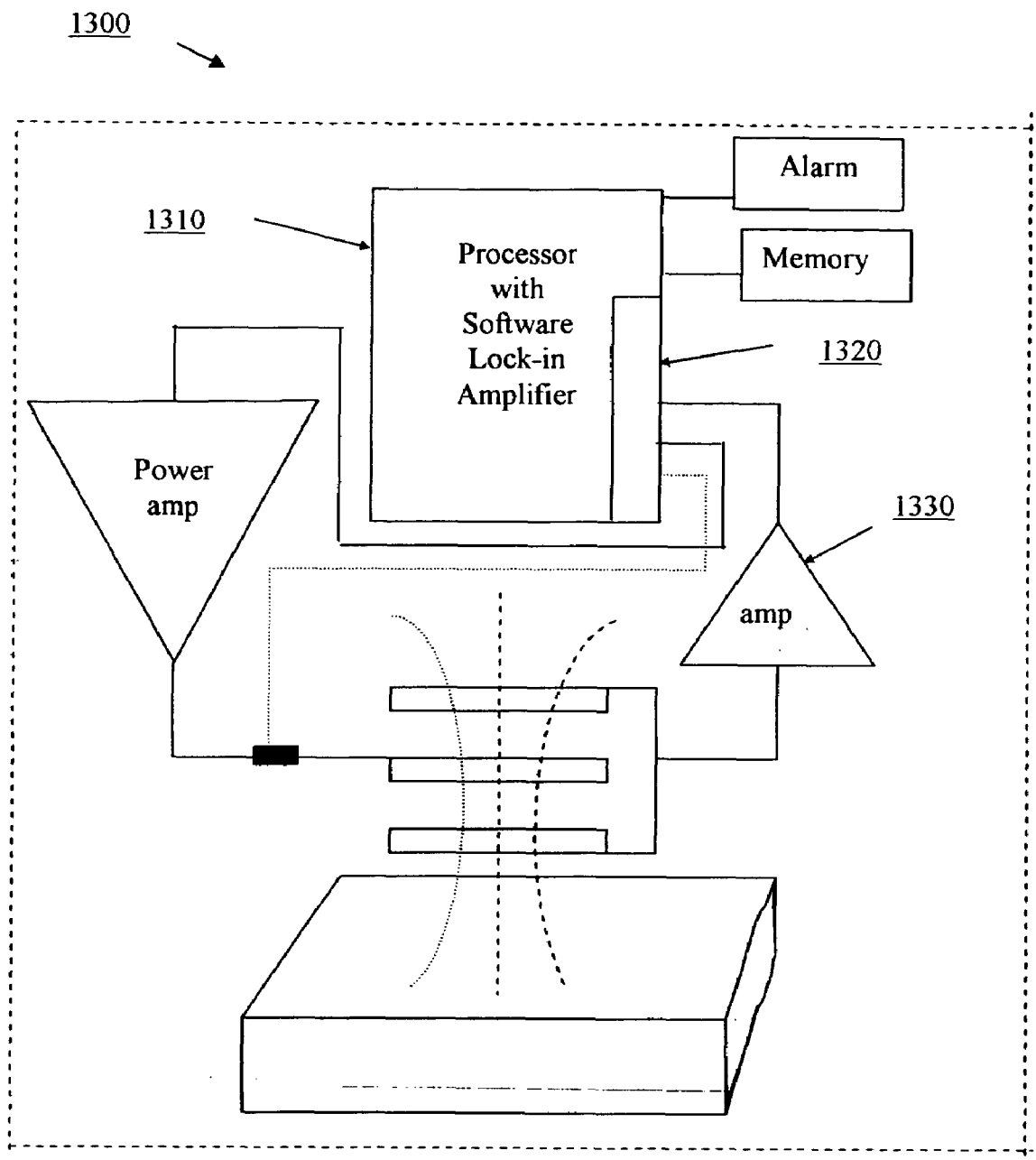
FIG. 13 is a block diagram of an exemplary embodiment of the electromagnetic inductance device for evaluation of fatigue utilizing a processor based lock-in amplifier.

FIG. 13 shows an example of the device 1300 utilizing processor based software lock-in amplifier 1310. A data acquisition board 1320 provides data exchange between the processor 1310 and amplifier 1330. This solution has significant advantages in terms of the cost, the size and flexibility. The device can be assembled in a single portable board. Customized software lock-in amplifier utilizing National Instrument, LabView v. 6.0.2 software may be used for this embodiment.

Figure 14:
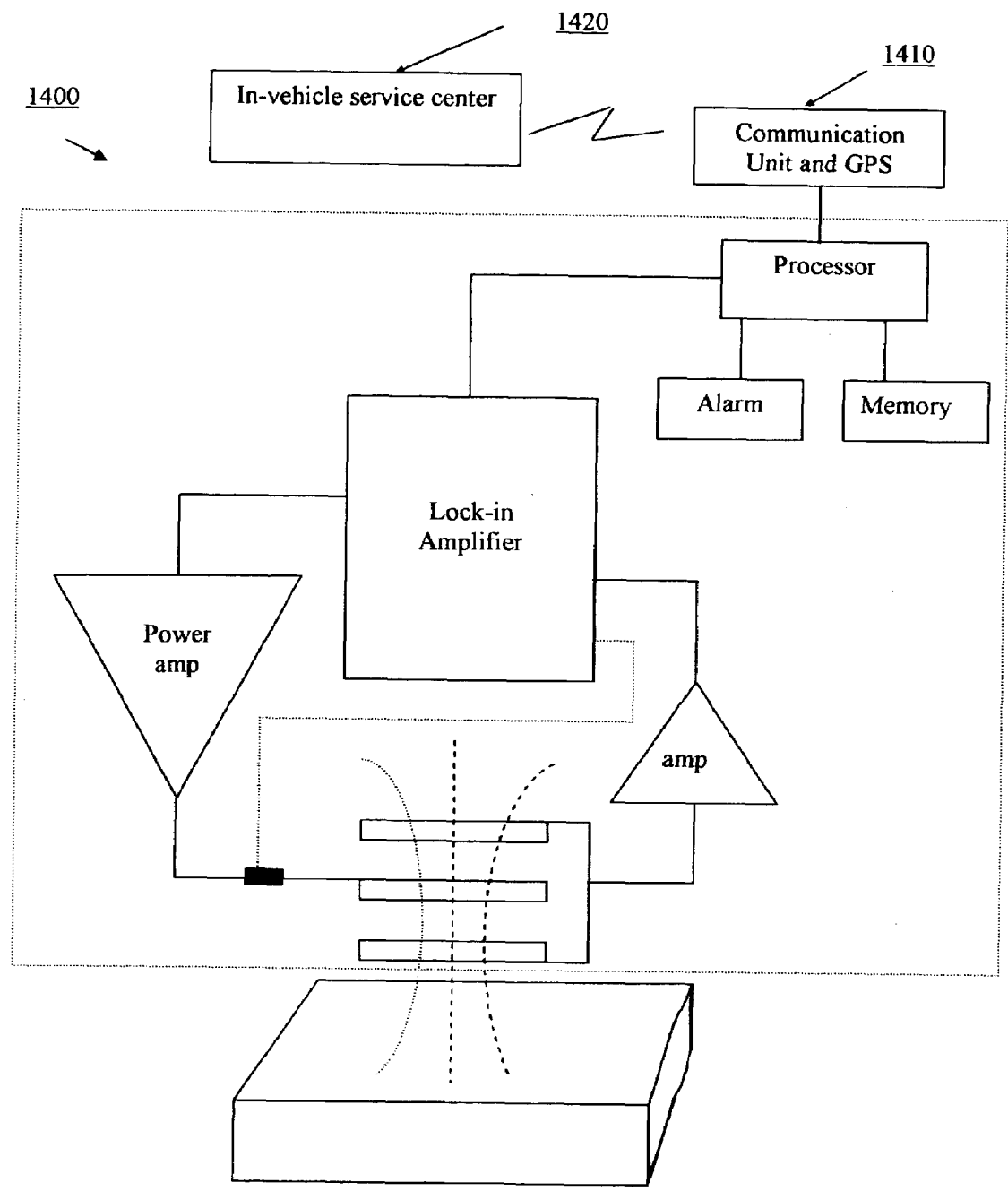
FIG. 14 is a block diagram of an exemplary embodiment of the electromagnetic inductance device for evaluation of fatigue, which is wirelessly connected to an in-vehicle service center (wake-up call).

As it's shown in FIG. 14, the device 1400 may be wirelessly 1410 connected to a call center (wake-up service) 1420. The device automatically connects the driver with an operator in the call center, when a drowsy condition is detected. The operator locates the vehicle using GPS data and navigates the driver to the nearest rest area while keeping him alert asking questions or asking to perform some simple physical operations.

What is claimed is:

1. A method for assessing fatigue of an operator comprising the steps of:
   a) placing an electromagnetic inductance device to be fixed to a vehicle's safety belt and positioned against a driver's chest;
   b) embedding another version of said device in the back of a driver's seat;
   c) connecting said electromagnetic inductance device to a vehicles's computer via a cable;
   d) passing an alternating current through an excitation coil;
   e) measuring at least one induced current waveform derived from a receiver coil;
   f) processing said at least one induced current waveform associated with changes in an amplitude caused by eddy current losses in a heart region;
   g) determining a fatigue level based on said changes in said eddy current.

2. The method of claim 1, wherein the act of processing said at least one induced current waveform comprises the step of:
   evaluating a heart rate (HR), a stroke volume (SV), and a cumulative index of a cardiac activity (CA).

3. The method of claim 2, wherein said CA is calculated by:

$$CA_i = k * Q_i \text{n.u.}$$

Where:
k is a normalizing factor for converting a calculated value of $Q_i$ to a value;
$Q_i$=area of a wave $W_i$;
n.u. stands for normalized unit.

4. The method of claim 3, wherein said $Q_i$ is calculated by:

$$Q_i = \sum_{j=1}^{n} A_j$$

Where:
$Q_i$=area of CA wave related to cardiac cycle i,
$A_j$=amplitude of sample j of CA wave of cardiac cycle i,
n=number of samples within cardiac cycle i.

5. The method of claim 1, wherein a fatigue level (F) is determined by:

$$F = LP/HP$$

Where
F=fatigue value,
LP=sympathetic activity power,
HP=parasympathetic activity power.

6. The method of claim 5, wherein said sympathetic activity power (LP) and said parasympathetic activity power (HP) is determined using a Fast Fourier Transform (FFT) algorithm.

7. The method of claim 5, wherein a baseline fatigue level pattern is determined during the first 30 minutes using a 5 minutes moving window with a 30 second increment.

8. The method of claim 7, wherein said pattern is updated every 5 minutes thus providing an adaptation to a changing driving environment.

9. The method of claim 1, wherein a transition from wakefulness to drowsing is characterized by a rapid shift of predominance of sympathetic activity to predominance of parasympathetic activity.

10. The method of claim 9, wherein a sympathetic activity power (LP) drops up to 10%, while a parasympathetic activity power (HP) increases up to 50% during time interval from 1 to 5 minutes.

11. The method of claim 9, further comprising the step of:
    calculating a mean ratio, $F_c$, of said sympathetic activity power and said parasympathetic activity power, LP/HP, respectively, for 5 minutes using data stored in a FIFO buffer and compares $F_c$ with a 30 minutes mean value $F_m$.

12. The method of claim 11, wherein if said $F_c \leq 0.75 * F_m$, then a system alarms a user.

13. The method of claim 1, further comprising the step of:
    warning a driver if the driver is drifting from wakefulness to drowsing.

14. The method of claim 13, wherein an intensity of said warning signal depends on a calculated length of an expected transition time from wakefulness to drowsing.

15. The method of claim 14, wherein said intensity gradually increases from lowest to highest level reflecting the expected transition time from equal or less than 60 s to less then 5 s.

16. The method of claim 13, wherein projected values of said fatigue level, F, is determined within next 60 seconds of driving.

17. The method of claim 16, wherein 10 last stored values of said fatigue level are smoothed using a 9-points triangular smooth method:

$$F_j = \frac{Y_{j-4} + 2Y_{j-3} + 3Y_{j-2} + 4Y_{j-1} + 5Y_j + 4Y_{j+1} + 3Y_{j+2} + 2Y_{j+3} + Y_{j+4}}{25}$$

Where:
$Y_j$=value of measurement j;
j=5 to n−4;
n=10.

18. The method of claim 17, wherein said smooth method comprises two iterations and transforms a fatigue level waveform in a vector representing a tendency of cardiac activity variability of a current driving pattern of the driver.

19. The method of claim 18, wherein a first of said two iterations has j=5, wherein a first pair of coordinates of said fatigue level for j=5 is equal to:

$$F_5 = \frac{Y_1 + 2Y_2 + 3Y_3 + 4Y_4 + 5Y_5 + 4Y_6 + 3Y_7 + 2Y_8 + Y_9}{25}$$
$$t = 5,$$

wherein a second of said two iterations has j=6, wherein a second pair of coordinates of said fatigue level for j=6 is equal to:

$$F_6 = \frac{Y_2 + 2Y_3 + 3Y_4 + 4Y_5 + 5Y_6 + 4Y_7 + 3Y_8 + 2Y_9 + Y_{10}}{25},$$
$$t = 6,$$

where t=measurement number.

20. The method of claim 18, wherein said vector is determined by:

$$F = A*t$$

Where:
F=fatigue level;
A=linear coefficient;
t=measurement number.

21. The method of claim 18, wherein the driver is drifting from wakefulness to drowsiness if said vector crosses a threshold line during 60 seconds after a last measurement.

22. The method of claim 21, wherein said threshold line is determined by:

$$Y = F_d$$

Where:

$$F_d = 0.75 * F_m.$$

* * * * *